United States Patent [19]

Deroose

[11] Patent Number: Plant 7,736

[45] Date of Patent: Dec. 3, 1991

[54] *FICUS BENJAMINA* PLANT NAMED REGINALD

[76] Inventor: Reginald Deroose, Droogte 139, 9050 Evergem, Belgium

[21] Appl. No.: 569,005

[22] Filed: Aug. 17, 1990

[51] Int. Cl.[5] ..... A01H 5/00

[52] U.S. Cl. ..... Plt./88

[58] Field of Search ..... Plt./88, 88.9

*Primary Examiner*—Howard J. Locker

*Attorney, Agent, or Firm*—Foley & Lardner

[57] ABSTRACT

A *Ficus benjamina* plant named 'Reginald' characterized by its yellow-green immature leaves, with dark green variegation of varying shape and amount at and extending from the midrib. As the leaves mature in age, the yellow-green main leaf color becomes a darker green, with the variegation always remaining a darker green than the main leaf color.

2 Drawing Sheets

1

The present invention comprises a new and distinct cultivar of *Ficus benjamina,* known by the cultivar name 'Reginald'.

'Reginald' is a mutation discovered by the inventor Reginald Deroose in 1986 in greenhouses in Evergem, Belgium. The new cultivar was discovered among plants of the parent cultivar *Ficus benjamina* 'Exotica' and was recognized due to its green-yellow leaf color and dark green foliage along the midrib of the leaf.

The first act of asexual reproduction of 'Reginald' was accomplished by tissue culture later in 1986 in a laboratory in Evergem, Belgium by applicant. Horticultural examination of 'Reginald' has demonstrated that the combination of characteristics as herein disclosed for the new cultivar are firmly fixed and are retained through successive generations of asexual reproduction, which can be performed by cuttings in addition to tissue culture.

'Reginald' has not been observed under all possible environmental conditions. The phenotype may vary significantly with variations in environment such as temperature, light intensity, and day length. The following observations, measurements and comparisons describe plants grown in Evergem, Belgium under greenhouse conditions which closely approximate those generally used in horticultural practice.

The following traits have been repeatedly observed to be characteristics which in combination distinguish 'Reginald' from other varieties of *Ficus benjamina* with which the inventor is familiar.

1. The leaf color of 'Reginald' is a fresh yellow-green, with dark green variegation of varying dimension near the midrib. The leaf color is totally different than the parent 'Exotica' which is dark green and also different from other variegated varieties of *F. benjamina* with which applicant is familiar. The main leaf color turns darker for interior leaves covered by new leaves. If leaves remain fully exposed to light or they mature they will maintain the fresh yellow-green color. This can be seen in Sheet 1 of the drawings where mature, fully exposed leaves are of the same color as newly forming leaves.

2. The leaf marking differs from all known *F. benjamina* varieties having variegated leaves. Along the midrib is a dark green irregular marking that occupies from about 5 to 20% of the leaf surface. The marking becomes darker as the leaf color darkens, but always remains slightly darker than the main leaf color.

2

In comparison to known cultivars, 'Reginald' is distinguished by its fresh yellow-green leaf color and the dark green variegation along the midrib of the leaf. The parent cultivar 'Exotica' has non-variegated dark green leaf color (slightly lighter than R.H.S. 147). The cultivar 'Golden King' has variegated leaves, but the main leaf color is a medium to dark green and the variegation is a light yellow appearing at the edges and inwardly of the edges.

All color references are measured against The Royal Horticultural Society Colour Chart. Colors are as closely approximate as possible. Color may vary somewhat depending on horticultural practices such as light level, temperature and fertilization rate, among others.

The accompanying color photographic drawings illustrate a typical specimen plant of 'Reginald', with photographic color depicting true colors to the extent possible with reproductions of this type.

Sheet 1 comprises a front perspective view of the new cultivar.

Sheet 2 comprises a closeup view showing in more detail the leaf variegation. The leaf color in Sheet 2 is much more green than the actual yellow-green quite accurately shown in Sheet 1. Sheet 2 is accordingly of primary value in illustrating the variegation patterns.

Origin: Mutation discovered among plants of tissue cultures *Ficus benjamina* 'Exotica'.

Classification: *Ficus benjamina* cv 'Reginald'.

Propagation: By cuttings or tissue culture.

Plant: (general description): The plant has the usual *Ficus benjamina* shape. The main stem is irregularly branched, with the branches being at an angle of 45° to 60° and the tips bending down.

Leaves:

- *Form.*—Elliptic to acuminate with a rather long pointed top.
- *Size.*—8 to 10 cm. long; 3.5 to 4 cm. wide.
- *Margin.*—Smooth.
- *Aspect.*—The surface of the leaf is slightly undulating or wavy.
- *Texture.*—Slightly glossy; luxuriant.
- *Petiole.*—About 1.5 to 2 cm. long.
- *Veins.*—A rather thick midrib and normal side veins extending from midrib to margin.
- *Variegation.*—Along the midrib are dark green irregular markings that occupy 5 to 20% of the leaf surface.

*Color.*—Upper surface: Fresh leaves are approximately 151A-B; as leaves mature and are exposed to less light due to the covering of new leaves, color becomes darker to 144A and 146A but remains lighter than the color of the leaves of the parent cultivar Exotica, which is slightly lighter than 147A; variegation remains approximately 146A but when upper surface of mature leaf is at its darkest, variegation is always slightly darker. At any particular time, there is a myriad of colors ranging from a very light yellow-green (151A) through a wide range of relatively darker green colors, depending on the degree of exposure of mature leaves to light. This, together with the dark midrib variegation, presents a very unique and pleasing appearance. Young leaf: R.H.S. 151A-B; variegation R.H.S. 146A. Older leaf: R.H.S. 144A; variegation R.H.S. 146A.

Oldest leaf: R.H.S. 146A but slightly lighter; variegation R.H.S. 146A but slightly darker. Lower surface: On fresh to mature to covered leaves, color remains within 144A-C range; variegation does not appear on lower surface. Upper surface midrib: R.H.S. 150A. Lower surface midrib: R.H.S. 150B-C. Petiole: In the young stage, slightly brown-red; later grey-green; dull green when fully mature.

Inflorescence: Insignificant.

Reproductive organs: Normal.

Roots: Good rooting system.

I claim:

1. A new and distinct cultivar of *Ficus benjamina* plant named 'Reginald', as illustrated and described.

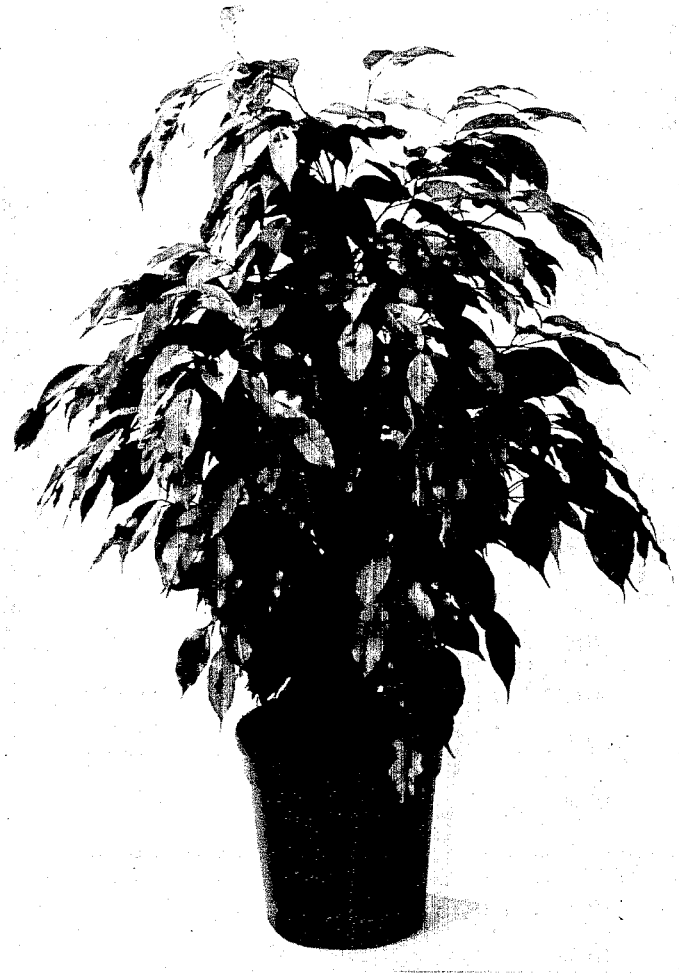

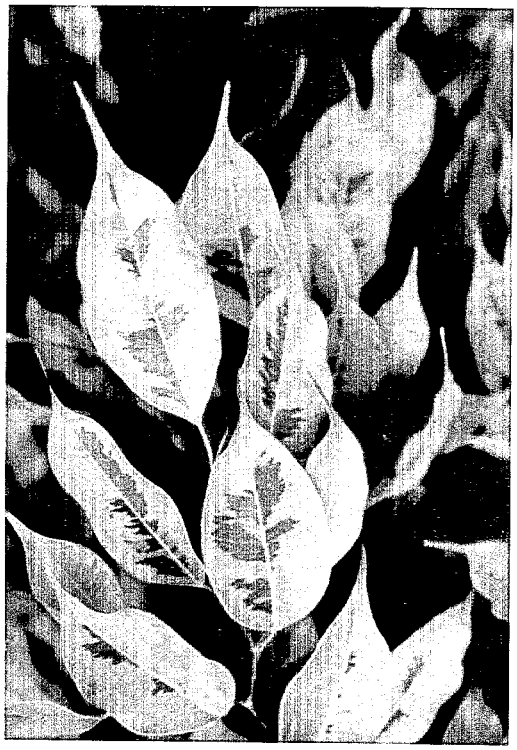

* * * * *